United States Patent
Li et al.

(10) Patent No.: US 10,807,938 B2
(45) Date of Patent: Oct. 20, 2020

(54) METHOD FOR PREPARING MALEATE BY SELECTIVE CATALYTIC OXIDATION OF LIGNIN

(71) Applicant: SOUTH CHINA UNIVERSITY OF TECHNOLOGY, Guangzhou (CN)

(72) Inventors: Xuehui Li, Guangzhou (CN); Zhenping Cai, Guangzhou (CN); Yingwen Li, Guangzhou (CN); Jinxing Long, Guangzhou (CN); Lefu Wang, Guangzhou (CN)

(73) Assignee: SOUTH CHINA UNIVERSITY OF TECHNOLOGY, Guangzhou (CN)

( * ) Notice: Subject to any disclaimer, the term of this patent is extended or adjusted under 35 U.S.C. 154(b) by 0 days.

(21) Appl. No.: 16/343,830

(22) PCT Filed: Dec. 14, 2016

(86) PCT No.: PCT/CN2016/109908
§ 371 (c)(1),
(2) Date: Jun. 30, 2019

(87) PCT Pub. No.: WO2018/072289
PCT Pub. Date: Apr. 26, 2018

(65) Prior Publication Data
US 2019/0322611 A1  Oct. 24, 2019

(30) Foreign Application Priority Data
Oct. 21, 2016  (CN) .......................... 2016 1 0920732

(51) Int. Cl.
| | | |
|---|---|---|
| *C07C 57/145* | (2006.01) | |
| *C07C 51/16* | (2006.01) | |
| *B01J 31/02* | (2006.01) | |

(52) U.S. Cl.
CPC ......... *C07C 57/145* (2013.01); *B01J 31/0285* (2013.01); *B01J 31/0298* (2013.01);
(Continued)

(58) Field of Classification Search
CPC ....... C07C 51/16; C07C 67/035; C07C 69/60; C07C 57/145; B01J 2231/70; B01J 31/34; B01J 31/0298; B01J 31/0285
See application file for complete search history.

(56) References Cited

U.S. PATENT DOCUMENTS

| | | | |
|---|---|---|---|
| 6,392,088 B1 * | 5/2002 | Bertola | C07C 67/08 560/190 |
| 8,394,973 B2 * | 3/2013 | Dubois | C07C 51/235 530/350 |

(Continued)

FOREIGN PATENT DOCUMENTS

| | | |
|---|---|---|
| CN | 103910699 | 7/2014 |
| CN | 105618139 | 6/2016 |

OTHER PUBLICATIONS

Crestini, C. et al., Immobilized methyltrioxo rhenium (MTO)/H2O2 systems for the oxidation of lignin and lignin model compounds, Bioorganic & Medicinal Chemistry, vol. 14, pp. 5292-5302 (Year: 2006).*

*Primary Examiner* — Yate' K Cutliff
(74) *Attorney, Agent, or Firm* — JMB Davis Ben-David

(57) ABSTRACT

The invention discloses a method for preparing maleate by selective catalytic oxidation of lignin. The method uses a heteropolyacid functionalized ionic liquid as a catalyst, and an aqueous alcohol solution as a reaction medium to achieve high-efficiency selective catalytic conversion and ring opening oxidation of biomass lignin at a reaction temperature of 110-160° C. and an oxygen pressure of 0.5-1.0 MPa for 1-6 h. The selectivity of maleate is higher than 47.83%. The yield and selectivity of a single chemical derived from the (Continued)

depolymerization of lignin in the present invention are much higher than the prior art, and the ionic liquid catalyst exhibits outstanding advantages such as availability of recovery and recycling through simple temperature adjustment; the reaction conditions of the present invention are mild, and the process is green and safe, easy to operate, and available for batch and continuous production. The invention provides a new green way for preparing bulk chemicals like maleate from reproducible raw materials such as lignin.

13 Claims, 2 Drawing Sheets

(52) U.S. Cl.
CPC ........... *C07C 51/16* (2013.01); *B01J 2231/70* (2013.01); *B01J 2531/002* (2013.01)

(56) References Cited

U.S. PATENT DOCUMENTS

| | | | | |
|---|---|---|---|---|
| 2014/0273104 A1* | 9/2014 | Paripati | ................. | C07C 59/185 |
| | | | | 435/99 |
| 2016/0135452 A1* | 5/2016 | Zhang | .................... | A01N 31/14 |
| | | | | 514/547 |

* cited by examiner

US 10,807,938 B2

METHOD FOR PREPARING MALEATE BY SELECTIVE CATALYTIC OXIDATION OF LIGNIN

CROSS-REFERENCE TO RELATED APPLICATIONS

This is the U.S. National Stage of International Patent Application No. PCT/CN2016/109908 filed Dec. 14, 2016, which was published in Chinese under PCT Article 21(2), and which in turn claims the benefit of Chinese Patent Application No. CN 201610920732.1 filed Oct. 21, 2016.

TECHNICAL FIELD

The invention relates to maleate, in particular to a method for preparing maleate by selective oxidation to open the ring of lignin by a heteropolyacid functionalized ionic liquid, and belongs to the technical field of high value utilization of biomass.

BACKGROUND ART

Biomass is the only carbon-containing reproducible resource currently discovered. Compared with fossil energy, biomass has the advantages of low sulfur content and zero $CO_2$ emission. The main components of biomass include cellulose, hemicellulose, and lignin. In recent years, high-performance conversion of cellulose and hemicellulose by chemical or biological methods to prepare biofuels and platform compounds has been well developed. As the second richest component of biomass, lignin molecule contains various functional groups such as hydroxyl group, aldehyde group, carboxyl group, ketone group, and carbon-carbon double bond. However, due to its structural complexity and uncertainty, how to convert lignin with high selectivity becomes the main technical problem of application of lignin.

In recent years, techniques including hydrogenolysis, liquefaction, alcoholysis, and pyrolysis have been widely used to convert lignin. For example, Xu et al. utilize formic acid as a hydrogen source and Pt/C as a catalyst to degrade organic dissolvable lignin in switchgrass in an ethanol solution. It is found that the system can promote the conversion of polymer compounds into small-molecule liquid products, and the reaction time may greatly influence the distribution of products and the properties of liquid products. After 4 h of reaction, 21% of the lignin was converted into 7 main products, after 20 h, the relative molecular mass of 76% of the lignin decreased. It was found by elemental analysis that the O/C ratio in the liquid product was reduced by 50% and the H/C ratio was increased by 10%. However, these conversion processes always require harsh reaction conditions with high temperature or pressure. In contrast, the conditions for catalytic oxidation of lignin are mild. Partenheimer et al. used Co/Mn/Zr/Br as a catalyst to oxidize lignin in air-aqueous acetic acid system to obtain 18 aromatic compounds such as p-hydroxybenzaldehyde, p-hydroxybenzoic acid, vanillin, vanillic acid, syringaldehyde and syringic acid. However, since lignin is a polymer having a 3D network structure crosslinked by a petroleum alkylphenol unit, when a solid catalyst is used to degrade lignin, it is difficult to contact the substrate, the reaction is difficult to carry out and the selectivity of depolymerized product is poor. Therefore, now it still remains a main challenge to improve the conversion rate of lignin and selectivity of the product during the utilization of lignin.

Maleic acid and its esters are important bulk chemical products. They are mainly derived from petrochemical industry, and the production methods thereof include benzene oxidation and butane oxidation. The former is gradually replaced by the latter due to the toxicity of the raw material. However, the raw materials of both benzene oxidation and butane oxidation relies on fossil resources, and the reaction conditions are harsh (for example, the butane method usually requires high temperature and high pressure). With the promotion of the concept of sustainable development, it is particularly important to prepare maleic acid (ester) by catalytic conversion of reproducible resources such as lignin under mild conditions.

SUMMARY OF THE INVENTION

In order to overcome the disadvantages and deficiencies of the prior art, the object of the present invention is to provide a method for preparing maleate by selective catalytic oxidation to open the ring of lignin. The method is environmentally friendly, can realize high-efficiency conversion of lignin, can use the catalyst repeatedly with high recovery rate.

The heteropolyacid functionalized ionic liquid catalyst used in the method overcomes the disadvantages of conventional ionic liquids like difficulty in recycling, and exhibit advantages of both homogeneous and heterogeneous catalysts. It has good catalytic efficiency, simple preparation method, recovery rate and no pollution to the environment, meantime achieving efficient conversion of lignin and separation of ionic liquid catalyst and the product.

The object of the invention may be achieved by the following technical solutions:

A method for preparing maleate by selective catalytic oxidation of lignin, comprising: adding lignin, a heteropolyacid functionalized ionic liquid, and an aqueous alcohol solution to a autoclave, and reacting at 110-160° C. under 0.5-1.0 MPa oxygen atmosphere for 1-5 h; after the reaction, centrifuging the reaction solution, conducting liquid-liquid separation to obtain maleate and the ionic liquid catalyst; wherein
the heteropolyacid functionalized ionic liquid consists of a cation and an anion; the cation includes a alkyl or alkanesulfonate imidazole cation or a pyridine, and the anion includes a phosphotungstate, a phosphomolybdate, a silicotungstate, and a silicomolybate.

To further realize the objects of the present invention, preferably, the cation has an alkyl chain length of C1-C6.

The heteropolyacid functionalized ionic liquid is prepared by the following steps:

Preferably, (1) weighing an equimolar amount of N-alkylimidazole and butane sultone and reacting at 30-50° C. for 12-24 h; after the reaction, washing with diethyl ether and drying under vacuum to obtain a white solid internal salt; wherein the N-alkylimidazole has a carbon chain length of C1-C6;

(2) dissolving the phosphotungstic acid in deionized water and stirring until completely dissolved; weighing a carbonate with half of the molar amount of phosphotungstic acid, slowly adding it to the phosphotungstic acid solution, stirring at room temperature to obtain a homogeneous solution; removing the solvent, and drying under vacuum for 12-48 h to obtain a heteropolyacid salt;

(3) weighing an equimolar amount of the heteropolyacid salt and the internal salt, completely dissolving them in deionized water to prepare two solutions respectively, adding the inner salt solution dropwise to the heteropolyacid salt solution with stirring, then stirring at room temperature for 12-48 h;

(4) after the reaction, removing the solvent by rotary evaporation, and drying the obtained solid under vacuum to obtain a heteropolyacid functionalized ionic liquid.

Preferably, said drying under vacuum of steps (1) and (2) is conducted at 40-60° C.; said drying the obtained solid under vacuum in step (4) is conducted at 60-80° C. in a vacuum drying oven for 12-48 h.

Preferably, the lignin is obtained by sufficiently drying a lignin raw material, pulverizing it to 40-60 mesh, washing the soluble component and the ash thereof with deionized water and sufficiently drying for use; mixing 1 part by mass of $H_2SO_4$ and 10-20 parts by mass of the treated lignin raw material thoroughly, adding 50-200 parts by mass of a 75% by volume aqueous ethanol solution, introducing an inert atmosphere, keeping the reaction temperature at 100-120° C., and after the reaction, conducting separation and vacuum drying; the lignin raw material includes bagasse, cassava, corn cobs, and corn stover.

Preferably, said stirring at room temperature lasts for 12-24 h.

Preferably, the alcohol in the aqueous alcohol solution is methanol, ethanol, n-propanol or isopropanol, and the volume concentration of the aqueous alcohol solution is 10-100%.

Preferably, the aqueous alcohol solution is used in an amount of 10-80 mL per gram of lignin, and the heteropolyacid functionalized ionic liquid is used in an amount of 0.5-3 mmol per gram of lignin.

Preferably, the ionic liquid catalyst is used after recovery.

201510778418X discloses a method for preparing vanillin by catalytic oxidative degradation of lignin, wherein the solid acid catalyst is a heteropolyacid, a salt thereof or a hydrate thereof, and the main product of the application is aromatic compound, which is mainly vanillin and is the same as traditional lignin oxidation process. The catalyst of the invention is a functionalized ionic liquid, wherein the cationic moiety contains a sulfonic acid functional group, and the anionic moiety is a heteropolyacid, which is completely different from the catalyst in 201510778418X; the target product of the present invention is mainly maleate (an aliphatic diester); the role of the catalyst is completely different in each case; and in the present invention the reaction conditions are more mild, the oxygen pressure is lower, and the yield of the product is higher.

Compared with the prior art, the present invention has the following advantages and beneficial effects:

(1) For the first time, a single chemical is obtained directly from lignin with high selectivity;

(2) High lignin conversion rate and product selectivity are achieved. The catalyst used in the invention has good catalytic activity, and the conversion rate of lignin and the selectivity of the maleic acid (ester) product are 92% and 73.21%, respectively;

(3) The preparation method of the catalyst is simple. The preparation of the catalyst can be conducted by a simple ion exchange method at normal temperature;

(4) The catalyst is easy to recover. The catalyst used in the present invention can directly recover by temperature adjustment, so the process is simple and the catalyst may be easily separated from the product.

(5) The reaction conditions are mild, the process is green and safe with simple operation and both batch and continuous production can be realized.

DETAILED DESCRIPTION OF THE EMBODIMENTS

In order to better understand the present invention, the present invention will be further described below in conjunction with the embodiments, but the embodiments of the present invention are not limited thereto.

Example 1

1. Preparation of Ionic Liquid $BSmimCuPW_{12}O_{40}$:

(1) Weighing an equimolar amount of N-methylimidazole and 1,4-butane sultone and reacting at 50° C. for 24 h; after the reaction, washing with diethyl ether and drying under vacuum at 60° C. to obtain a white solid internal salt;

(2) dissolving the phosphotungstic acid in deionized water, stirring until the phosphotungstic acid is completely dissolved; weighing basic copper carbonate with half of the molar amount of phosphotungstic acid, slowly adding to the phosphotungstic acid solution, stirring at room temperature for 24 h to obtain a light blue solution; then removing the solvent by a rotary evaporator at 80° C., conducting vacuum drying at 60° C. for 12 h to obtain a heteropolyacid $CuHPW_{12}O_{40}$;

(3) weighing an equimolar amount of the heteropolyacid $CuHPW_{12}O_{40}$ and the inner salt prepared in step (1), dissolving the heteropolyacid $CuHPW_{12}O_{40}$ and the inner salt in deionized water, respectively, then dropwise adding the inner salt solution to the heteropolyacid $CuHPW_{12}O_{40}$ solution with stirring, and allowing them to react at room temperature for 48 h;

(4) after the reaction, removing the solvent by rotary evaporation to obtain a blue solid, drying under vacuum at 60° C. for 48 h to obtain the heteropolyacid functionalized ionic liquid, namely 1-(4-sulfobutyl)-3-methylimidazolium phosphotungstate copper salt ionic liquid ($BSmimCuPW_{12}O_{40}$).

2. Preparation of Bagasse Lignin:

(1) Pretreatment of agricultural waste: after the bagasse is sufficiently dried, pulverizing it to below 60 mesh by mechanical pulverization, washing the soluble component and ash thereof with deionized water and sufficiently drying the bagasse for use;

(2) Extraction of organic dissolvable lignin: mixing 1 part by mass of $H_2SO_4$ and 15 parts by mass of bagasse thoroughly, introducing an inert atmosphere, and keeping the reaction temperature at 120° C.; after the reaction, conducting separation and vacuum drying to obtain high purity bagasse lignin.

Figure 1:
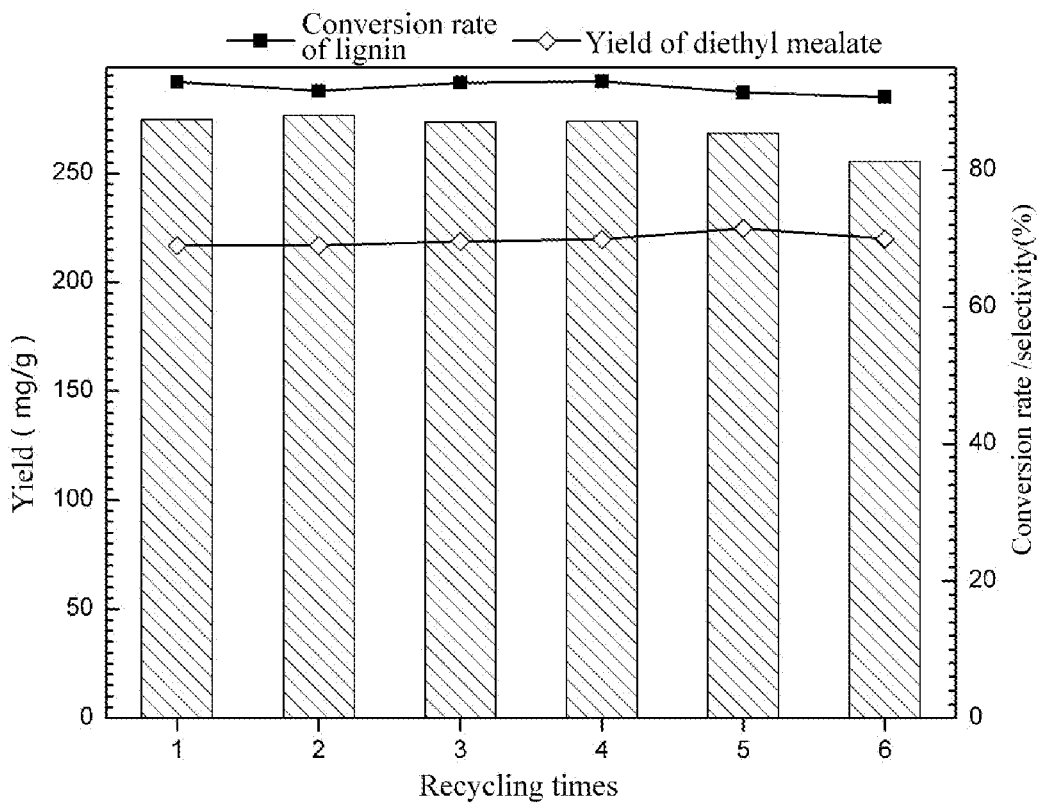
FIG. 1 shows the recycling performance of the 1-(4-sulfobutyl)-3-methylimidazolium phosphotungstate copper salt ionic liquid catalyst in Example 1.
Figure 2:
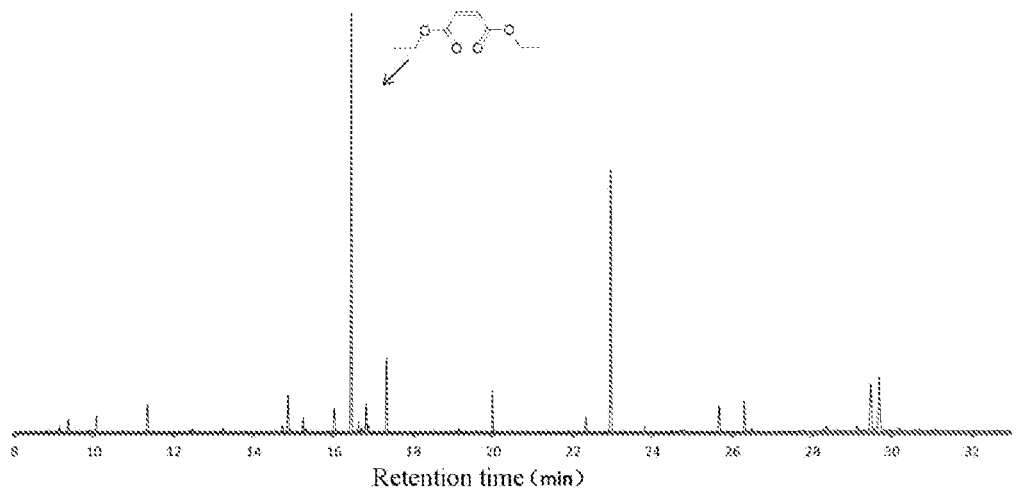
FIG. 2 is a GC-MS diagram of the lignin catalytic oxidation product in Example 1.
Figure 3:
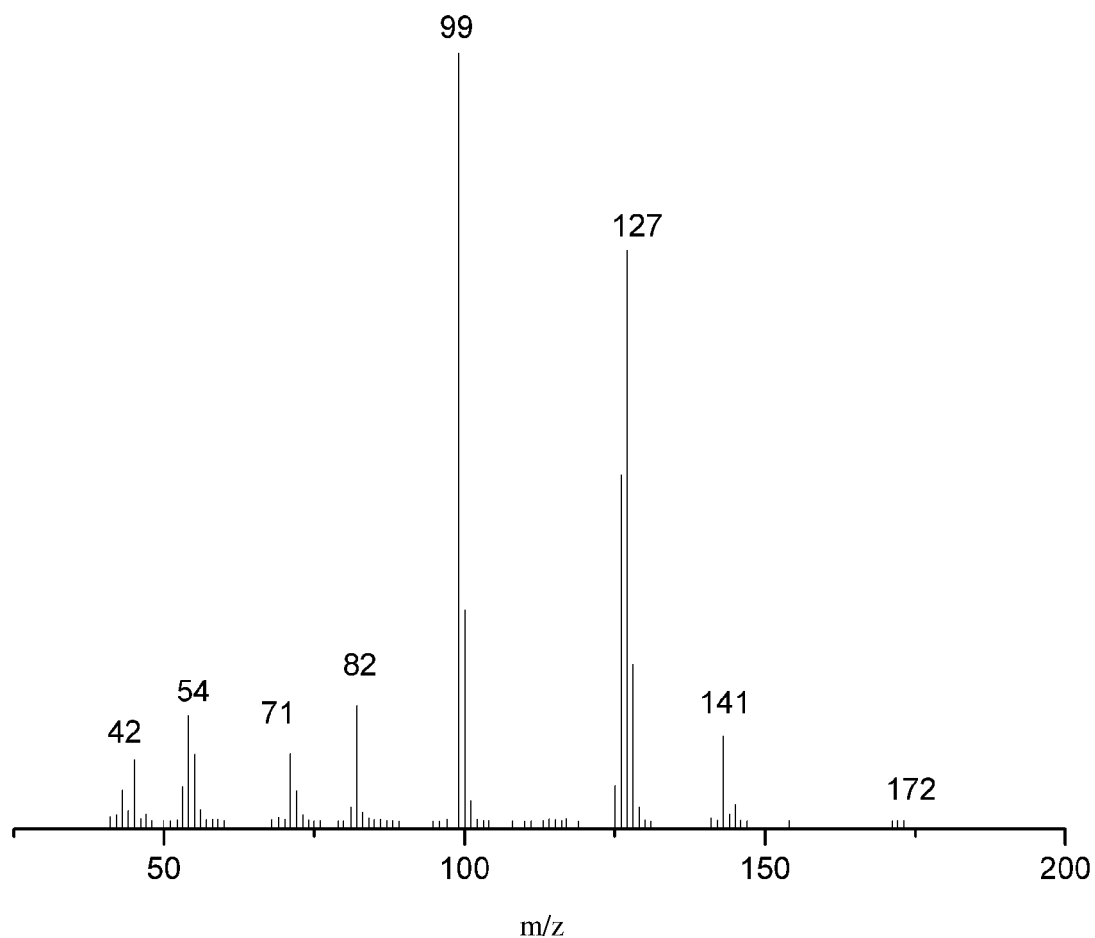
FIG. 3 is a mass spectrum of diethyl maleate, the main product of lignin catalytic oxidation in Example 1.

3. Method for Selective Catalytic Oxidation of Lignin:

Accurately weighing 0.25 g bagasse lignin, 20 mL 80% (volume concentration) aqueous ethanol solution, 0.9 mmol 1-(4-sulfobutyl)-3-methylimidazolium phosphotungstate copper salt ionic liquid ($BSmimCuPW_{12}O_{40}$) in a 100 mL autoclave, sealing it, replacing the atmosphere with high purity oxygen for 5 times, pressurizing to 0.8 MPa, and reacting at 160° C. for 5 h. After the reaction, cooling the mixture, and centrifuging to obtain the ionic liquid catalyst, which is then vacuum-dried at 60° C. for 24 hours. The catalyst was used for the catalyst cycle performance test, and after the catalyst was used for 5 times, no significant decrease of the catalytic activity was observed (FIG. 1). The ionic liquid supernate was made up to 25 mL, and 10 mL of the made up solution was added to 25 mL of deionized water to precipitate unreacted lignin. The lignin conversion rate is calculated by the ratio of the mass difference between the lignin raw material and unreacted lignin to the mass of the lignin raw material. The product of catalytic oxidation of lignin was qualitatively analyzed by GC/MS (FIG. 2 and FIG. 3) and quantified by gas chromatography. The selectivity of diethyl maleate is obtained from the ratio between the mass obtained by gas chromatography and the mass of all products. After the test, it was found that the lignin conversion rate was 90.7%, and the yield and selectivity of diethyl maleate were 153.60 mg/g and 59.32%, respectively.

The method of the invention discloses obtaining maleate directly from the catalytic oxidation of lignin for the first time. Compared with the current lignin treating process, it has advantages of mild reaction conditions, green and safe reaction process, high conversion rate of raw material, high product yield and selectivity (currently catalytic depolymerization products of lignin are mainly phenolic compounds, the highest yield of which is 23%, and single compound selectivity of which is less than 30%), easy recovery of the catalyst with high recovery rate and good recyclability, and availability of batch and continuous production.

Example 2

The difference between Example 2 and Example 1 is:
1. Preparation of Ionic Liquid 1-(4-sulfobutyl)-3-ethylimidazolium phosphotungstate Nickel salt BSeimNiPW$_{12}$O$_{40}$:
(1) Weighing an equimolar amount of N-ethylimidazole and 1,4-butane sultone and reacting at 30° C. for 18 h; after the reaction, washing with diethyl ether and drying under vacuum at 50° C. to obtain a white solid internal salt;
(2) dissolving the phosphotungstic acid in deionized water, stirring until the phosphotungstic acid is completely dissolved; weighing Nickel carbonate with half of the molar amount of phosphotungstic acid, slowly adding to the phosphotungstic acid solution, stirring at room temperature for 18 h; then removing the solvent by a rotary evaporator at 70° C., conducting vacuum drying at 50° C. for 48 h to obtain a heteropolyacid NiHPW$_{12}$O$_{40}$;
(3) weighing an equimolar amount of the heteropolyacid NiHPW$_{12}$O$_{40}$ and the inner salt prepared in step (1), dissolving the heteropolyacid NiHPW$_{12}$O$_{40}$ and the inner salt in deionized water, respectively, then dropwise adding the inner salt solution to the heteropolyacid NiHPW$_{12}$O$_{40}$ solution with stirring, and allowing them to react at room temperature for 48 h;
(4) after the reaction, removing the solvent by rotary evaporation to obtain a solid, and drying under vacuum at 70° C. for 36 h to obtain the heteropolyacid functionalized ionic liquid BSeimNiPW$_{12}$O$_{40}$;
3. Method for Selective Oxidation of Bagasse Lignin:
Accurately weighing 0.5 g bagasse lignin, 50 mL 70% (volume concentration) aqueous ethanol solution, 1.8 mmol 1-(4-sulfobutyl)-3-ethylimidazolium phosphotungstate Nickel salt ionic liquid (BSeimCuPW$_{12}$O$_{40}$) in a 100 mL autoclave, sealing it, replacing the atmosphere with high purity oxygen for 5 times, pressurizing to 0.8 MPa, and reacting at 160° C. for 5 h. After the reaction, cooling the mixture, and centrifuging to obtain the ionic liquid catalyst, which is then vacuum-dried at 60° C. for 24 hours. The ionic liquid supernate was made up to 25 mL, and 10 mL of the made up solution was added to 25 mL of deionized water to precipitate unreacted lignin. The lignin conversion rate was 77.9%. Another 10 mL of the made up solution was used for composition analysis in the same manner as in Example 1. The yield and selectivity of dimethyl maleate were 71.61 mg/g and 58.84%, respectively.

Example 3

The difference between Example 3 and Example 1 is:
1. Preparation of Ionic Liquid 1-(4-sulfobutyl)-3-methylimidazolium Phosphotungstate Manganese Salt BSmimMnPW$_{12}$O$_{40}$:
(1) Weighing an equimolar amount of N-methylimidazole and 1,4-butane sultone and reacting at 50° C. for 24 h; after the reaction, washing with diethyl ether and drying under vacuum at 60° C. to obtain a white solid internal salt;
(2) dissolving the phosphotungstic acid in deionized water, stirring until the phosphotungstic acid is completely dissolved; weighing Manganese carbonate with half of the molar amount of phosphotungstic acid, slowly adding to the phosphotungstic acid solution, stirring at room temperature for 24 h; then removing the solvent by a rotary evaporator, conducting vacuum drying at 80° C. for 30 h to obtain a heteropolyacid MnHPW$_{12}$O$_{40}$;
(3) weighing an equimolar amount of the heteropolyacid MnHPW$_{12}$O$_{40}$ and the inner salt prepared in step (1), dissolving the heteropolyacid NiHPW$_{12}$O$_{40}$ and the inner salt in deionized water, respectively, then dropwise adding the inner salt solution to the heteropolyacid MnHPW$_{12}$O$_{40}$ solution with stirring, and allowing them to react at room temperature for 48 h;
(4) after the reaction, removing the solvent by rotary evaporation to obtain a solid, and drying under vacuum at 70° C. for 36 h to obtain the heteropolyacid functionalized ionic liquid BSmimMnPW$_{12}$O$_{40}$;
3. Method for Selective Oxidation of Bagasse Lignin:
Accurately weighing 0.25 g corn stover lignin, 20 mL 30% (volume concentration) aqueous ethanol solution, 0.9 mmol 1-(4-sulfobutyl)-3-ethylimidazolium phosphotungstate Manganese salt ionic liquid (BSmimMnPW$_{12}$O$_{40}$) in a 100 mL autoclave, sealing it, replacing the atmosphere with high purity oxygen for 5 times, pressurizing to 1.0 MPa, and reacting at 140° C. for 5 h. After the reaction, cooling the mixture, and centrifuging to obtain the ionic liquid catalyst, which is then vacuum-dried at 60° C. for 24 hours. The ionic liquid supernate was made up to 25 mL, and 10 mL of the made up solution was added to 25 mL of deionized water to precipitate unreacted lignin. The lignin conversion rate was 80.9%. Another 10 mL of the made up solution was used for composition analysis in the same manner as in Example 1. The yield and selectivity of diethyl maleate were 87.65 mg/g and 67.36%, respectively.

Example 4

The difference between Example 4 and Example 1 is:
1. Preparation of Ionic Liquid 1-(4-sulfobutyl)-3-butylimidazolium Phosphotungstate Sodium Salt BSbimNa$_2$PW$_{12}$O$_{40}$:
(1) Weighing an equimolar amount of N-butylimidazole and 1,4-butane sultone and reacting at 40° C. for 24 h; after the reaction, washing with diethyl ether and drying under vacuum at 60° C. to obtain a white solid internal salt;

(2) dissolving the phosphotungstic acid in deionized water, stirring until the phosphotungstic acid is completely dissolved; weighing Sodium carbonate with half of the molar amount of phosphotungstic acid, slowly adding to the phosphotungstic acid solution, stirring at room temperature for 24 h; then removing the solvent by a rotary evaporator, conducting vacuum drying at 60° C. for 36 h to obtain a heteropolyacid $Na_2HPW_{12}O_{40}$;

(3) weighing an equimolar amount of the heteropolyacid $Na_2HPW_{12}O_{40}$ and the inner salt prepared in step (1), dissolving the heteropolyacid $Na_2HPW_{12}O_{40}$ and the inner salt in deionized water, respectively, then dropwise adding the inner salt solution to the heteropolyacid $Na_2HPW_{12}O_{40}$ solution with stirring, and allowing them to react at room temperature for 48 h;

(4) after the reaction, removing the solvent by rotary evaporation to obtain a solid, and drying under vacuum at 80° C. for 14 h to obtain the heteropolyacid functionalized ionic liquid $BSbimNa_2PW_{12}O_{40}$;

3. Method for Selective Oxidation of Bagasse Lignin:

Accurately weighing 0.25 g bagasse lignin, 20 mL 70% (volume concentration) aqueous ethanol solution, 0.9 mmol 1-(4-sulfobutyl)-3-butylimidazolium phosphotungstate Sodium salt ionic liquid ($BSbimNa_2PW_{12}O_{40}$) in a 100 mL autoclave, sealing it, replacing the atmosphere with high purity oxygen for 5 times, pressurizing to 0.8 MPa, and reacting at 160° C. for 5 h. After the reaction, cooling the mixture, and centrifuging to obtain the ionic liquid catalyst, which is then vacuum-dried at 60° C. for 24 hours. The ionic liquid supernate was made up to 25 mL, and 10 mL of the made up solution was added to 25 mL of deionized water to precipitate unreacted lignin. The lignin conversion rate was 81.3%. Another 10 mL of the made up solution was used for composition analysis in the same manner as in Example 1. The yield and selectivity of diethyl maleate were 53.62 mg/g and 77.50%, respectively.

Example 5

The difference between Example 5 and Example 1 is:
Method for Selective Oxidation of Bagasse Lignin:

Accurately weighing 1.0 g bagasse lignin, 20 mL 80% (volume concentration) aqueous ethanol solution, 0.9 mmol 1-(4-sulfobutyl)-3-methylimidazolium phosphotungstate copper salt ionic liquid ($BSmimCuPW_{12}O_{40}$) in a 100 mL autoclave, sealing it, replacing the atmosphere with high purity oxygen for 5 times, pressurizing to 0.5 MPa, and reacting at 150° C. for 5 h. After the reaction, cooling the mixture, and centrifuging to obtain the ionic liquid catalyst, which is then vacuum-dried at 60° C. for 24 hours. The ionic liquid supernate was made up to 25 mL, and 10 mL of the made up solution was added to 25 mL of deionized water to precipitate unreacted lignin. The lignin conversion rate was 83.2%. Another 10 mL of the made up solution was used for composition analysis in the same manner as in Example 1. The yield and selectivity of diethyl maleate were 38.38 mg/g and 48.33%, respectively.

Example 6

The difference between Example 6 and Example 1 is:
Method for Selective Oxidation of Bagasse Lignin:

Accurately weighing 0.25 g bagasse lignin, 20 mL 80% (volume concentration) aqueous ethanol solution, 0.9 mmol 1-(4-sulfobutyl)-3-methylimidazolium phosphotungstate copper salt ionic liquid ($BSmimCuPW_{12}O_{40}$) in a 100 mL autoclave, sealing it, replacing the atmosphere with high purity oxygen for 5 times, pressurizing to 0.8 MPa, and reacting at 160° C. for 4 h. After the reaction, cooling the mixture, and centrifuging to obtain the ionic liquid catalyst, which is then vacuum-dried at 60° C. for 24 hours. The ionic liquid supernate was made up to 25 mL, and 10 mL of the made up solution was added to 25 mL of deionized water to precipitate unreacted lignin. The lignin conversion rate was 88.3%. Another 10 mL of the made up solution was used for composition analysis in the same manner as in Example 1. The yield and selectivity of diethyl maleate were 133.41 mg/g and 60.18%, respectively.

Example 7

The difference between Example 7 and Example 1 is:
Method for Selective Oxidation of Bagasse Lignin:

Accurately weighing 0.25 g bagasse lignin, 20 mL 80% (volume concentration) aqueous ethanol solution, 1.5 mmol 1-(4-sulfobutyl)-3-methylimidazolium phosphotungstate copper salt ionic liquid ($BSmimCuPW_{12}O_{40}$) in a 100 mL autoclave, sealing it, replacing the atmosphere with high purity oxygen for 5 times, pressurizing to 0.8 MPa, and reacting at 160° C. for 6 h. After the reaction, cooling the mixture, and centrifuging to obtain the ionic liquid catalyst, which is then vacuum-dried at 60° C. for 24 hours. The ionic liquid supernate was made up to 25 mL, and 10 mL of the made up solution was added to 25 mL of deionized water to precipitate unreacted lignin. The lignin conversion rate was 93.1%. Another 10 mL of the made up solution was used for composition analysis in the same manner as in Example 1. The yield and selectivity of diethyl maleate were 142.31 mg/g and 61.25%, respectively.

Example 8

The difference between Example 8 and Example 1 is:
Method for Selective Oxidation of Bagasse Lignin:

Accurately weighing 0.25 g cassava lignin, 20 mL 100% (volume concentration) aqueous ethanol solution, 0.9 mmol 1-(4-sulfobutyl)-3-methylimidazolium phosphotungstate copper salt ionic liquid ($BSmimCuPW_{12}O_{40}$) in a 100 mL autoclave, sealing it, replacing the atmosphere with high purity oxygen for 5 times, pressurizing to 0.8 MPa, and reacting at 160° C. for 5 h. After the reaction, cooling the mixture, and centrifuging to obtain the ionic liquid catalyst, which is then vacuum-dried at 60° C. for 24 hours. The ionic liquid supernate was made up to 25 mL, and 10 mL of the made up solution was added to 25 mL of deionized water to precipitate unreacted lignin. The lignin conversion rate was 82.3%. Another 10 mL of the made up solution was used for composition analysis in the same manner as in Example 1. The yield and selectivity of diethyl maleate were 95.71 mg/g and 47.83%, respectively.

Example 9

The difference between Example 9 and Example 1 is:
Method for Selective Oxidation of Bagasse Lignin:

Accurately weighing 0.25 g dealkali lignin, 20 mL 100% (volume concentration) aqueous ethanol solution, 0.9 mmol 1-(4-sulfobutyl)-3-methylimidazolium phosphotungstate copper salt ionic liquid ($BSmimCuPW_{12}O_{40}$) in a 100 mL autoclave, sealing it, replacing the atmosphere with high purity oxygen for 5 times, pressurizing to 0.8 MPa, and reacting at 160° C. for 5 h. After the reaction, cooling the mixture, and centrifuging to obtain the ionic liquid catalyst, which is then vacuum-dried at 60° C. for 24 hours. The ionic liquid supernate was made up to 25 mL, and 10 mL of the made up solution was added to 25 mL of deionized water to precipitate unreacted lignin. The lignin conversion rate was 92.3%. Another 10 mL of the made up solution was used for composition analysis in the same manner as in Example 1. The yield and selectivity of diethyl maleate were 162.22 mg/g and 73.21%, respectively.

Example 10

The difference between Example 10 and Example 1 is:
Method for Selective Oxidation of Bagasse Lignin:
Accurately weighing 0.25 g bagasse lignin, 20 mL 100% (volume concentration) aqueous ethanol solution, 0.9 mmol 1-(4-sulfobutyl)-3-methylimidazolium phosphotungstate copper salt ionic liquid (BSmimCuPW$_{12}$O$_{40}$) in a 100 mL autoclave, sealing it, replacing the atmosphere with high purity oxygen for 5 times, pressurizing to 0.8 MPa, and reacting at 160° C. for 5 h. After the reaction, cooling the mixture, and centrifuging to obtain the ionic liquid catalyst, which is then vacuum-dried at 60° C. for 24 hours. The ionic liquid supernate was made up to 25 mL, and 10 mL of the made up solution was added to 25 mL of deionized water to precipitate unreacted lignin. The lignin conversion rate was 96.5%. Another 10 mL of the made up solution was used for composition analysis in the same manner as in Example 1. The yield and selectivity of diethyl maleate were 147.33 mg/g and 57.15%, respectively.

The embodiments of the present invention are not limited to the above-described embodiments, and any other changes, modifications, substitutions, combinations, and simplifications that are made without departing from the spirit and scope of the present invention should be equivalent and within the scope of the invention.

What is claimed is:

1. A method for preparing maleate by selective catalytic oxidation of lignin, comprising: adding lignin, a heteropolyacid functionalized ionic liquid, and an aqueous alcohol solution to a autoclave, and reacting at 110-160° C. under 0.5-1.0 MPa oxygen atmosphere for 1-5 h; after the reaction, centrifuging the reaction solution, conducting liquid-liquid separation to obtain maleate and the ionic liquid catalyst; wherein
the heteropolyacid functionalized ionic liquid consists of a cation and an anion; the cation consists of at least one member selected from a alkyl or alkanesulfonate imidazole cation or a pyridine, and the anion consists of at least one member selected from a-phosphotungstate, a phosphomolybdate, a silicotungstate, and a silicomolybate.

2. The method for preparing maleate by selective catalytic oxidation of lignin according to claim 1, wherein the cation has an alkyl chain length of C1-C6.

3. The method for preparing maleate by selective catalytic oxidation of lignin according to claim 1, wherein the heteropolyacid functionalized ionic liquid is prepared by the following steps:
(1) weighing an equimolar amount of N-alkylimidazole and butane sultone and reacting at 30-50° C. for 12-24 h; after the reaction, washing with diethyl ether and drying under vacuum to obtain a white solid internal salt; wherein the N-alkylimidazole has a carbon chain length of C1-C6;
(2) dissolving the phosphotungstic acid in deionized water and stirring until completely dissolved; weighing a carbonate with half of the molar amount of phosphotungstic acid, slowly adding it to the phosphotungstic acid solution, stirring at room temperature to obtain a homogeneous solution; removing the solvent, and drying under vacuum for 12-48 h to obtain a heteropolyacid salt;
(3) weighing an equimolar amount of the heteropolyacid salt and the internal salt, completely dissolving them in deionized water to prepare two solutions respectively, adding the inner salt solution dropwise to the heteropolyacid salt solution with stirring, then stirring at room temperature for 12-48 h;
(4) after the reaction, removing the solvent by rotary evaporation, and drying the obtained solid under vacuum to obtain a heteropolyacid functionalized ionic liquid.

4. The method for preparing maleate by selective catalytic oxidation of lignin according to claim 3, wherein said drying under vacuum of steps (1) and (2) is conducted at 40-60° C.; said drying the obtained solid under vacuum in step (4) is conducted at 60-80° C. in a vacuum drying oven for 12-48 h.

5. The method for preparing maleate by selective catalytic oxidation of lignin according to claim 3, wherein the lignin is obtained by sufficiently drying a lignin raw material, pulverizing it to 40-60 mesh, washing the soluble component and the ash thereof with deionized water and sufficiently drying for use; mixing 1 part by mass of H$_2$SO$_4$ and 10-20 parts by mass of the treated lignin raw material thoroughly, adding 50-200 parts by mass of a 75% by volume aqueous ethanol solution, introducing an inert atmosphere, keeping the reaction temperature at 100-120° C., and after the reaction, conducting separation and vacuum drying; and the lignin raw material consists of at least one member selected from bagasse, cassava, corn cobs, and corn stover.

6. The method for preparing maleate by selective catalytic oxidation of lignin according to claim 3, wherein said stirring at room temperature lasts for 12-24 h.

7. The method for preparing maleate by selective catalytic oxidation of lignin according to claim 1, wherein the alcohol in the aqueous alcohol solution is methanol, ethanol, n-propanol or isopropanol, and the volume concentration of the aqueous alcohol solution is 10-100%.

8. The method for preparing maleate by selective catalytic oxidation of lignin according to claim 1, wherein the aqueous alcohol solution is used in an amount of 10-80 mL per gram of lignin, and the heteropolyacid functionalized ionic liquid is used in an amount of 0.5-3 mmol per gram of lignin.

9. The method for preparing maleate by selective catalytic oxidation of lignin according to claim 1, wherein the ionic liquid catalyst is used after recovery.

10. The method for preparing maleate by selective catalytic oxidation of lignin according to claim 2, wherein the heteropolyacid functionalized ionic liquid is prepared by the following steps:
(1) weighing an equimolar amount of N-alkylimidazole and butane sultone and reacting at 30-50° C. for 12-24 h; after the reaction, washing with diethyl ether and drying under vacuum to obtain a white solid internal salt; wherein the N-alkylimidazole has a carbon chain length of C1-C6;
(2) dissolving phosphotungstic acid in deionized water and stirring until completely dissolved; weighing a carbonate with half of the molar amount of the phosphotungstic acid, slowly adding it to the phosphotungstic acid solution, stirring at room temperature to obtain a homogeneous solution; removing the solvent, and drying under vacuum for 12-48 h to obtain a heteropolyacid salt;

(3) weighing an equimolar amount of the heteropolyacid salt and the internal salt, completely dissolving them in deionized water to prepare two solutions respectively, adding the inner salt solution dropwise to the heteropolyacid salt solution with stirring, then stirring at room temperature for 12-48 h;

(4) after the reaction, removing the solvent by rotary evaporation, and drying the obtained solid under vacuum to obtain a heteropolyacid functionalized ionic liquid.

11. The method for preparing maleate by selective catalytic oxidation of lignin according to claim 10, wherein said drying under vacuum of steps (1) and (2) is conducted at 40-60° C.; said drying the obtained solid under vacuum in step (4) is conducted at 60-80° C. in a vacuum drying oven for 12-48 h.

12. The method for preparing maleate by selective catalytic oxidation of lignin according to claim 10, wherein the lignin is obtained by sufficiently drying a lignin raw material, pulverizing it to 40-60 mesh, washing the soluble component and the ash thereof with deionized water and sufficiently drying for use; mixing 1 part by mass of $H_2SO_4$ and 10-20 parts by mass of the treated lignin raw material thoroughly, adding 50-200 parts by mass of a 75% by volume aqueous ethanol solution, introducing an inert atmosphere, keeping the reaction temperature at 100-120° C., and after the reaction, conducting separation and vacuum drying; and the lignin raw material consists of at least one member selected from bagasse, cassava, corn cobs, and corn stover.

13. The method for preparing maleate by selective catalytic oxidation of lignin according to claim 10, wherein said stirring at room temperature lasts for 12-24 h.

* * * * *